US 6,555,060 B1

(12) United States Patent
Mauchan et al.

(10) Patent No.: US 6,555,060 B1
(45) Date of Patent: Apr. 29, 2003

(54) APPARATUS FOR PERFORMING DIAGNOSTIC TESTING

(75) Inventors: Donald E. Mauchan, Marlboro, MA (US); Philip R. Norris, North Reading, MA (US); Leonard Polizzotto, Stow, MA (US)

(73) Assignee: Polaroid Corporation, Waltham, MA (US)

( * ) Notice: Subject to any disclaimer, the term of this patent is extended or adjusted under 35 U.S.C. 154(b) by 0 days.

(21) Appl. No.: 09/417,297

(22) Filed: Oct. 13, 1999

Related U.S. Application Data

(60) Provisional application No. 60/104,150, filed on Oct. 14, 1998.

(51) Int. Cl.[7] .............................................. G01N 21/64
(52) U.S. Cl. ................... 422/52; 422/82.08; 422/82.05; 250/361 C
(58) Field of Search ............................. 422/52, 82.05, 422/82.08; 250/361 C, 458.1, 459.1

(56) References Cited

U.S. PATENT DOCUMENTS

| | | | |
|---|---|---|---|
| 3,390,962 A | 7/1968 | Goldsmith | 23/253 |
| 3,415,361 A | 12/1968 | Adams, Jr. et al. | 206/47 |
| 3,680,967 A | 8/1972 | Engelhardt | 356/246 |
| 3,788,205 A | 1/1974 | Pasieka et al. | 95/93 |
| 3,865,548 A | 2/1975 | Padawer | 23/230 |
| 4,111,754 A | 9/1978 | Park | 195/127 |
| 4,233,029 A | 11/1980 | Columbus | 23/230 |
| 4,254,083 A | 3/1981 | Columbus | 422/55 |
| 4,264,560 A | 4/1981 | Natelson | 422/58 |
| 4,271,119 A | 6/1981 | Columbus | 422/50 |
| 4,302,313 A | 11/1981 | Columbus | 204/195 R |
| 4,310,399 A | 1/1982 | Columbus | 204/195 R |
| 4,319,842 A * | 3/1982 | Priarone et al. | 250/458.1 |
| 4,323,536 A | 4/1982 | Columbus | 422/56 |
| 4,371,498 A | 2/1983 | Scordato et al. | 422/102 |
| 4,396,579 A | 8/1983 | Schroeder et al. | 422/52 |
| 4,413,407 A | 11/1983 | Columbus | 29/825 |
| 4,426,451 A | 1/1984 | Columbus | 436/518 |
| 4,439,526 A | 3/1984 | Columbus | 436/180 |
| 4,510,393 A | 4/1985 | Sell et al. | 250/475 |
| 4,549,952 A | 10/1985 | Columbus | 204/416 |
| 4,587,221 A | 5/1986 | Cais et al. | 436/500 |
| 4,608,231 A | 8/1986 | Witty et al. | 422/61 |
| 4,675,299 A | 6/1987 | Witty et al. | 436/165 |
| 4,757,004 A | 7/1988 | Houts et al. | 435/7 |
| 4,772,453 A | 9/1988 | Lisenbee | 422/52 |
| 4,797,259 A | 1/1989 | Matkovich et al. | 422/101 |
| 4,833,087 A | 5/1989 | Hinckley | 435/287 |
| 4,863,689 A | 9/1989 | Leong et al. | 422/52 |
| 4,879,097 A * | 11/1989 | Whitehead et al. | 356/389 |
| 4,906,439 A | 3/1990 | Grenner | 422/56 |
| 4,918,025 A | 4/1990 | Grenner | 436/165 |
| 4,948,564 A | 8/1990 | Root et al. | 422/101 |
| 4,948,975 A | 8/1990 | Erwin et al. | 250/361 |
| 4,954,714 A * | 9/1990 | Pollak et al. | 250/458.1 |
| 4,959,324 A | 9/1990 | Ramel et al. | 436/169 |
| 4,973,549 A | 11/1990 | Khanna et al. | 435/11 |
| 4,978,502 A | 12/1990 | Dole et al. | 422/58 |
| 4,985,631 A | 1/1991 | Wannlund et al. | 250/361 |
| 4,987,085 A | 1/1991 | Allen et al. | 324/407 |
| 5,011,663 A | 4/1991 | Innocenti | 422/102 |
| 5,035,866 A | 7/1991 | Wannlund | 422/102 |
| 5,063,090 A | 11/1991 | Wannlund | 427/384 |
| 5,073,484 A | 12/1991 | Swanson et al. | 435/7.92 |
| 5,075,077 A | 12/1991 | Durley, III et al. | 422/56 |
| 5,093,268 A | 3/1992 | Leventis et al. | 436/172 |

(List continued on next page.)

FOREIGN PATENT DOCUMENTS

| WO | WO 97/27463 | 7/1997 |

*Primary Examiner*—Jeffrey Snay

(57) ABSTRACT

The present invention relates to a hand-held diagnostic testing system and method employing apparatus that can effect a chemiluminescent reaction and record the same on photographic film.

16 Claims, 6 Drawing Sheets

U.S. PATENT DOCUMENTS

| | | | |
|---|---|---|---|
| 5,098,661 A | 3/1992 | Froehlich et al. | 422/102 |
| 5,100,621 A | 3/1992 | Berke et al. | 422/61 |
| 5,132,086 A | 7/1992 | Allen et al. | 422/56 |
| 5,159,197 A | 10/1992 | Wannlund | 250/328 |
| 5,164,301 A | 11/1992 | Thompson et al. | 435/29 |
| 5,167,922 A | 12/1992 | Long | 422/58 |
| 5,188,965 A | 2/1993 | Wannlund | 436/165 |
| 5,219,762 A | 6/1993 | Katamine et al. | 436/518 |
| 5,223,218 A * | 6/1993 | Fukuoka et al. | 250/361 C |
| 5,244,630 A | 9/1993 | Khalil et al. | 422/52 |
| 5,319,436 A | 6/1994 | Manns et al. | 356/246 |
| 5,332,549 A | 7/1994 | MacIndoe, Jr. | 422/63 |
| 5,355,215 A | 10/1994 | Schroeder et al. | 356/317 |
| 5,411,893 A | 5/1995 | Eden et al. | 436/165 |
| 5,418,171 A | 5/1995 | Kimura et al. | 436/518 |
| 5,441,894 A | 8/1995 | Coleman et al. | 436/518 |
| 5,457,527 A | 10/1995 | Manns et al. | 356/246 |
| 5,460,778 A | 10/1995 | Macindoe, Jr. | 422/63 |
| 5,482,839 A | 1/1996 | Ashihara et al. | 435/7.9 |
| 5,552,276 A | 9/1996 | Mochida | 435/6 |
| 5,657,118 A | 8/1997 | Lee | 356/246 |
| 5,772,967 A * | 6/1998 | Wannlund et al. | 356/244 |
| 5,833,923 A * | 11/1998 | McClintock et al. | 422/52 |

* cited by examiner

APPARATUS FOR PERFORMING DIAGNOSTIC TESTING

CROSS-REFERENCE TO RELATED APPLICATION

This application claims the benefit of Provisional Application No. 60/104,150, filed Oct. 14, 1998.

The present invention U.S. non-provisional patent application, Ser. No. 09/412,845, entitled "Diagnostic Assay System and Method; filed on Oct. 6, 1999, now U.S. Pat. No. 6,331,715.

BACKGROUND OF THE INVENTION

The present invention relates generally to diagnostic assay systems and methods capable for multiple samples in a simple and reliable manner.

A wide variety of systems and approaches exist which allow the occurrence and recording of luminescent reactions, such as of the chemiluminescent, or fluorescent type for qualitative and quantitative results. One class of analytical instruments typically used in this field is referred to as luminometers. Luminometers conduct and record luminescent reactions generated, for instance, by a biological test fluid sample that contains a reagent of interest, such as an analyte, and a reagent in an assay element. Examples of these approaches include single-sample luminometers fitted with photographic multipliers; single-sample luminometers fitted with solid-state detectors; multiple sample luminometers; automatic luminometers with imaging systems based on CCD cameras; and photographic camera type luminometers. Some of the foregoing devices using photographic films of the conventional and self-developing type for recording luminescent activity are described in, for example, in U.S. Pat. Nos. 4,863,689; 5,035,866; and 5,188,965. Heretofore known prior art, tends to be limited in a number of ways, such as being expensive due to the expensive electronics required, training of personnel required because of their relatively complicated nature, and being relatively cumbersome in use and expensive in construction.

Despite the existence of a wide variety of known diagnostic luminescent type testing systems and approaches, however, it is, nevertheless, desired to improve upon the overall ease, versatility, and reliability of such systems and their testing procedures, as well as reduce overall costs associated with their construction and use.

SUMMARY OF THE INVENTION

In accordance with the present invention, one provision is, preferably, made for a hand-held, portable diagnostic assay system. The system is operable for conducting and recording luminescent reactions, that generate luminescent signals, such as chemiluminescent and fluorescent signals, that are recordable an image recording medium, such as a film assemblage of the self-developing type. Included in the system, in one embodiment, is a housing assembly defining a light-tight enclosure carrying at least the film unit and an exposure opening that optically communicates the film unit and the luminescent read-out signal. A film processing unit in the housing is operable for processing exposed self-developing film units passing therethrough. Provision is made for a sample carrier means or assembly that has one condition for receiving a luminescent testing assembly and a second condition for exposing the film. The sample carrier assembly can carry, in a light-tight manner, at least one luminescent testing assembly that is capable of generating a luminescent read-out signal recordable on the image recording medium in response to the testing assembly being actuated. Whenever the sample carrier is in the second condition, the generated signal exposes the film unit. Developing the resultant latent image is initiated when the film unit is advanced from the housing after passing through the film processing unit.

In an illustrated preferred embodiment, the sample carrier has an opening for receiving a test container of the luminescent testing assembly. The test container comprises a reservoir that stores a luminescent testing means; which in a preferred embodiment is in the form of a fluid that is sealed by means of a sealing device. A portion of the reservoir is transparent for allowing transmission of the generated read-out signal to the film through an open exposure opening. A sampling device of the luminescent testing assembly can sample a surface to be tested and is inserted, in a light-tight manner, within the test container such that a portion thereof is immersed in the fluid. If the sampling device contains a reagent that reacts with a reagent in the assay fluid, the generated luminescent signal can expose the film through the open exposure opening and transparent portion. In this embodiment, movement of the sample carrier carrying the luminescent testing assembly opens the exposure opening and registers the transparent reservoir portion therewith for exposing the film. Movement of the sample carrier back to the receiving position closes the exposure opening. Further in another illustrated embodiment, the test container includes opaque means therein which serves, when the container is held in the sample carrier, to block ambient light from reaching the exposure opening.

In another illustrated preferred embodiment, provision is made for effecting and recording a luminescent read-out signal of a control test generally simultaneously with a luminescent signal of the test sample.

In an illustrated embodiment, a sample carrier assembly carries a luminescent sample test assembly and a luminescent control test assembly. Fluid transfer means, such as light-tight capillary grooves, allow transfer of the control and test fluids from separate ports therefor to the respective test assemblies. When the sample carrier is inserted into a recess in a processor housing containing the film, a shuttering mechanism is opened which allows luminescent read-out signals emitted from the test sample and control luminescent testing assemblies to respectively expose the film. Removal of the sample carrier from the processor housing closes the shutter. The film can be advanced as indicated above in the other embodiments.

In still another illustrated embodiment of the present invention, provision is made for a means and method for achieving a quantification of the luminescent signal generated and recorded on the film. In one such embodiment, such quantification is achieved by reason of an optical filter. The filter can have alternating light attenuating zones, such as transparent and opaque zones that act to delineate different sized read-out signals. The different sized images correlate to corresponding different test results. Because of the light attenuation, different sized luminescent images will be visible through correspondingly different sized attenuation zones; thereby providing a visual measurement of the test results. In yet other embodiments, the quantification can be obtained by pre-exposing the film with a gradation of different sized images. The different sizes correspond to different predetermined outputs of the luminescent signals. Alternately, provision is for a film overlay comprising a series of different sized images thereon with each overlay image corresponding to different test outputs. In use the test image that is captured during the actual test can be compared to images on the overlay for quantifying the test result.

Methods are contemplated for conducting and recording read-out signals that can expose the image recording material.

It is an object of the present invention to provide an improved method and system for conducting and recording luminescent reactions, wherein the results can be immediately and reliably ascertained by an operator.

It is another object of the present invention to provide an improved method and system for conducting and recording luminescent reactions in a hand-held assay processor using self-developing type film.

It is another object of the present invention to provide an improved method and system of the last noted types for conducting and recording multiple sample tests.

It is another object of the present invention to provide an improved method and system for conducting and recording luminescent reactions in a hand-held assay processor wherein both test sample and control fluids are applied to corresponding different test strips.

It is another object of the present invention to provide an improved method and system of the last noted types for conducting and recording luminescent reactions wherein the output signals are recorded on film and quantified.

It is another object of the present invention to detect the luminescent signals electronically and print relevant information on the film.

It is another object of the present invention to provide for an improved method and system which is simple and reliable to operate and which is low-cost in cost.

The above and other objects and features of the present invention will become apparent when reading the following description taken conjunction with the accompanying drawings wherein like parts are indicated by like reference numerals throughout the several views.

BRIEF DESCRIPTION OF THE DRAWINGS

FIG. 1A is an enlarged and fragmented schematic view of a film assemblage that can be used in connection with the invention;

DETAILED DESCRIPTION

Figure 1:
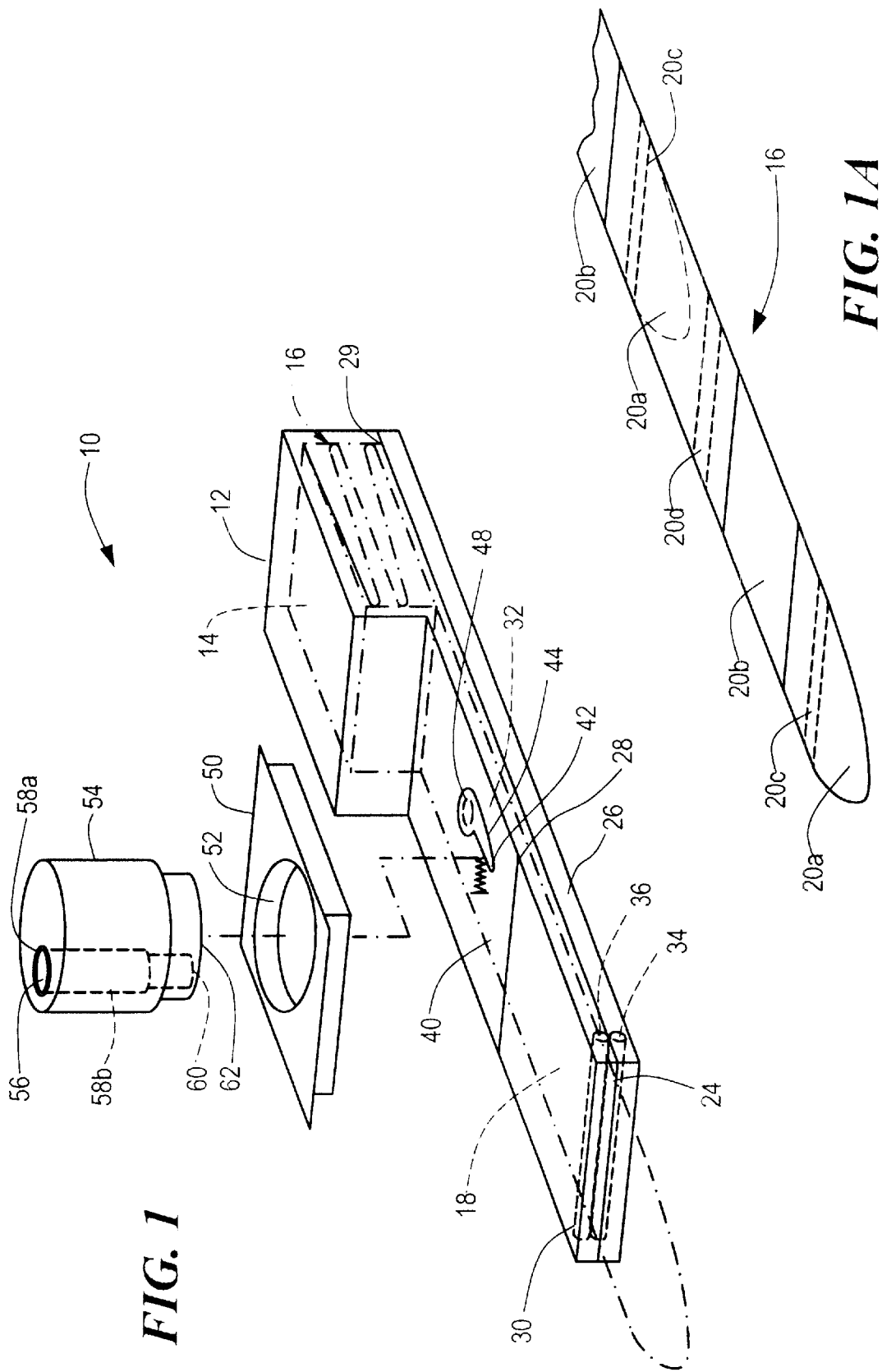
FIG. 1 is an exploded perspective schematic view illustrating several components forming one embodiment of a multiple sample diagnostic assay system of the present invention.
Figures 2, 3:
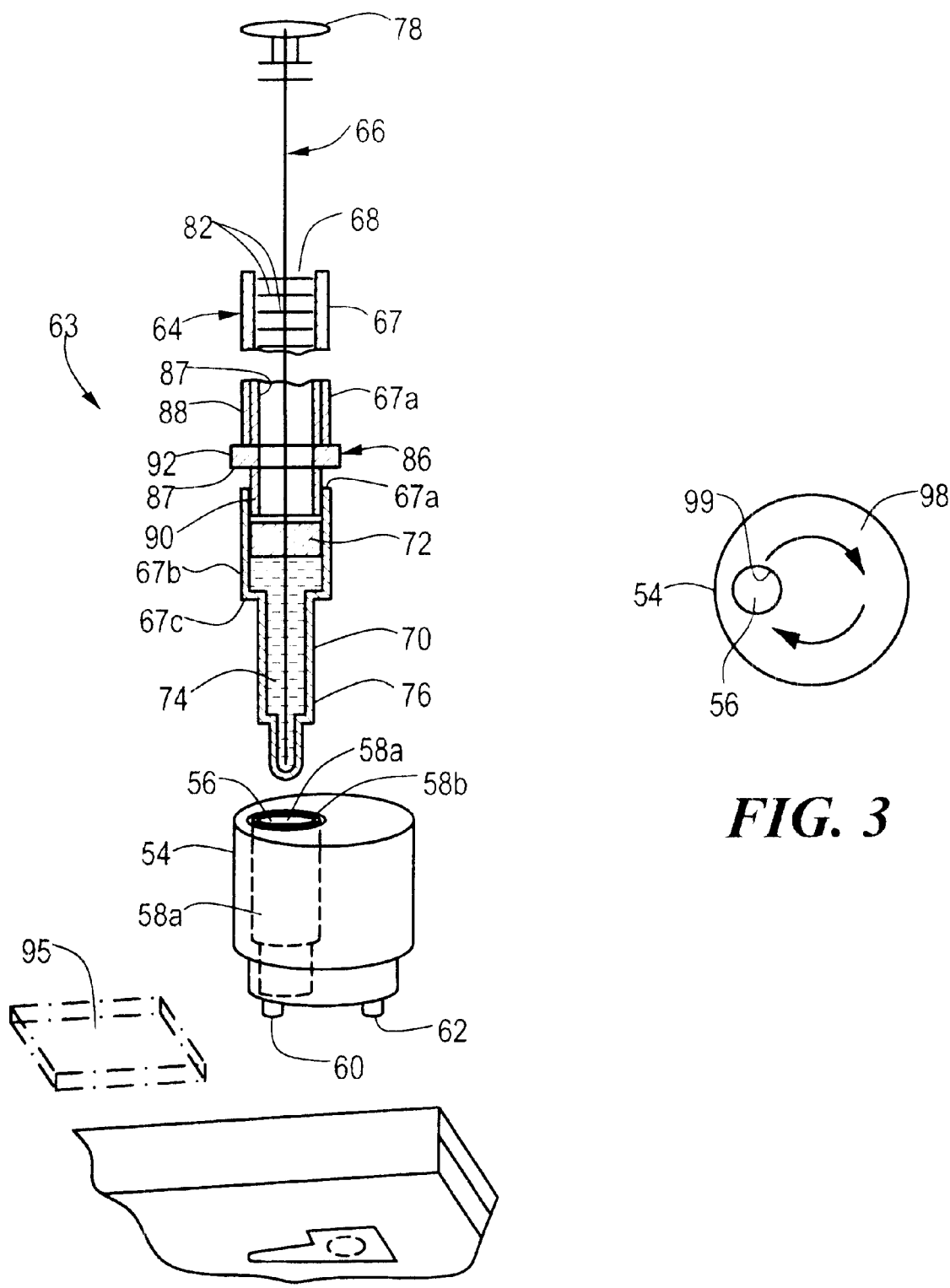
FIG. 2 is a schematic exploded perspective view illustrating components of the assay system.
FIG. 3 is a bottom plan view of a sample carrier component of the assay system.

Reference is made to FIGS. 1–3 for schematically illustrating one of the preferred embodiments of a multiple sample diagnostic assay system 10. The diagnostic assay 10 includes a light-tight, processor housing assembly 12 having the general configuration depictedu and containing therewithin a film box 14. Contained in light-tight relationship to the film box 14 is a film assemblage 16.

The preferred embodiment of the film assemblage 16 is similar to that described in copending and commonly assigned U.S. patent applications Ser. No. 08/738,772; and Ser. No. 08/829,914 a description thereof is incorporated herein and made a part hereof. Since the construction of the film assemblage does not, per se, form and aspect of the present invention, only those details of such a film assemblage needed for describing the present invention will be set forth. Details of such a construction are set forth in the aforenoted copending patent application. Basically, the film assemblage 16 includes an elongated strip 18 comprising a plurality of self-developing film units 20 secured end-to-end to connection strips in alternating arrangement to form a longitudinal strip. Weakened portions in the connection strips are structurally weakened to permit easy separation in a manner to be described. Each of the film units is, preferably, of the integral self-developing integral type. In this connection, each of the film units 20 includes a tab or leader portion 20a, an image recording area 20b, a pod 20c of processing fluid located at a leading end portion, and a fluid trap 20d at a trailing end. The photosensitive image recording area 20b is positioned within the housing assembly so as to be exposed to a read-out signal of a luminescent activity. Luminescent activity or read-out as used in this specification includes any luminescent activity such as of the chemiluminescent type, fluorescence, infrared and other signals that are recordable on an image recording material. The pod 20c is positioned adjacent the processing means, as will be described and a tab or leader portion 20a of the leading film unit protrudes from a film exit 24 in the device so that the film unit may be manually grasped for pulling and processing of the film unit as will be described. The film exit 24 is appropriately provided with flaps (not shown) or the like for providing a light-tight enclosure.

In the illustrated embodiment, the processor housing assembly 12 includes a pair of generally rectangular and matable lower and upper plate-like processor housing portions 26 and 28. The housing portions are hingedly connected as at 29 to permit loading of the film box within a complementary shaped compartment within the processor. The housing assembly 12 is, preferably, dimensioned to be hand-held and portable for providing a self-contained and portable diagnostic assay system that is convenient to use. The housing portions 26 and 28 can be made of any material suitable to define, preferably, a light-tight enclosure 32. While a hinged coupling is described, a wide variety of approaches for joining the two opposed housing components are envisioned. The lower processor housing portion 26 is similar in construction to that described in the last-noted application and basically includes a film supporting wall (not shown) a processing fluid spreading structure 30 (not shown) for spreading the processing fluid ruptured from the pod in a well-known manner. A lower spread roller 34 is rotatably supported in the lower housing portion for cooperating with a biased upper spread roller 36 in the upper housing portion 28 to define a pressure nip. The rollers 34 and 36 serve to rupture the pod and spread the processing fluid as a film unit passes therethrough. In addition, the nip acts to inexpensively retain the film assemblage 16 within the housing prior to use of the device. Accordingly, the film can be transported and handled without fear of it becoming dislodged or otherwise separated.

The upper housing 28 includes a generally rectangular recess 40 that has pivotally mounted thereon, as at 42, a shutter blade 44. The shutter blade 44 moves between light blocking and unblocking relationships relative to an exposure opening 48 that is in optical communication with an image portion of a film unit. A light-seal plate 50 has a construction as shown to be mounted in and suitably secured to reside within the recess of the upper housing and includes an aperture 52. The plate 50 serves to rotatably mount, within the aperture 52 a rotatable test sample carrier 54. The test sample carrier 54 has a generally cylindrical configuration with a reduced diameter portion that has a snug, light-tight fit within the plate. The test sample carrier 54 includes a passage 56 extending longitudinally therethrough. A plurality of linearly spaced apart stepped shoulders 58a, 58b are provided in the passageway for supporting a test sample device. A pair of arcuately spaced apart and downwardly protruding opening and closing pins 60 and 62; respectively, on the test sample carrier alternately engage the shutter to open and closed positions as the carrier is rotated in opposite directions; in a manner to be described. In this embodiment, the sample carrier can be manually grasped about its periphery and turned in either direction. Of course, manual means, such as handles or motorized means can be used to rotate the sample carrier.

The device 10 is adapted for particular use in connection with a luminescent assay testing assembly 63 that includes an ampoule 64 and a test sample pick-up device 66 that is housed and cooperates with the ampoule in a manner to be described. It will be understood, however, that the test system to be described is but one of several which can be used in conjunction with the device. In the illustrated embodiment, the luminescent testing assay assembly including the ampoule, fluid, and pick-up device are similar to that commercially available from Biotrace, Inc., Plainsboro, N.J. It will be understood that the device of the present invention can be used in connection with other similar diagnostic systems. The ampoule 64 includes a generally hollow tubular housing for slidably receiving the pick-up device 66. Preferably, the housing is made of transparent plastic, and has an open end portion 68 that is adapted to receive the sample pick-up, and a closed end portion 70. While the present embodiment of the ampoule includes a transparent housing, it will be appreciated that need not be the case. In the latter regard, however, the closed end portion should be transparent in order to transmit any luminescent activity; whereby the latter can form a latent image on the film. A sealing membrane 72 is located generally transversely to the housing 67 so as to define a chamber or reservoir 74 with the closed end portion in order to sealingly accommodate an assay fluid 76. The sealing membrane 72 is made of a thin-walled metallic material that is impervious to fluid and ambient atmosphere. The sealing membrane is adapted to be punctured by the sample pick-up device 66; when the latter is inserted therethrough. The assay fluid 76 can be one that generates a chemiluminescent signal in response to a reagent, such as ATP (Adenosine Triphosphate) being present on the sampling rings. ATP is used as an indicator of the presence of organic debris, such as microorganisms. The fluid 76 can be, for example, a Firefly reagent which generates a light signal in response to ATP collected on the sampling device 66. The sample pick-up device includes a handle 78, a stem 80 and a plurality of laterally extending sampling rings 82. The sampling rings 82 are used to engage a surface to be tested for microorganisms. A user merely rubs the rings against a surface to be tested, for instance, a food preparation surface and inserts the sampling ring into and through the membrane, whereupon the rings are immersed into the assay fluid. If ATP is present, in significant amounts on the sampling rings, it will react with the reagent in the fluid and generate a luminescent read-out signal that is recordable on the film. It is, of course, realized that the present invention contemplates use of a wide variety of fluids, membranes and sample pick-ups. The foregoing materials provide, but one of many that can be used in the context of the present invention.

Reference is made in particular to FIG. 2, wherein the luminescent testing assembly 63 is provided with an opaque means in the form of a plastic collar 86 being formed in combination with a segmented the tubular housing 67. The plastic collar 86 has a central axially extending passageway 87 through which the sample pick-up 66 is inserted. An upper end portion 88 is fit within a central passage of upper tubular portion 67a and a lower end portion 90 is fit within a lower portion 67b of the housing above the sealing membrane. A projecting rim 92 extends radially from the collar and is adapted to rest on the shoulder 67a.

In operation, a user can, for example, wipe the sampling rings on a surface to be tested for the presence of ATP. The ampoule housing 67 is placed within the passage 56 with the shoulder 58b being engaged by the collar rim 92 and the shoulder 58a engaging a surface 67c of the housing wherein the transparent closed end portion enters a reduced diameter portion of the passage 56, whereby the ampoule is in an upstanding position with respect to the sample carrier.

Prior to testing, the sample carrier is in a non-exposing mode, whereby the passage 56 is circumferentially spaced from the aperture and the shutter blade is in the closed condition. To commence testing, the user inserts the test sample device 66 through the membrane so that the sampling rings are immersed within the assay fluid to initiate a chemiluminescent reaction, if the test ATP reacts with the reagent in the assay fluid; after a preselected time interval. The time interval, of course, varies as a function of several factors not relevant to the present invention. Timing such intervals is accomplished by means of a suitable timer 95 mounted on the device in any appropriate fashion and in exposing relationship (not shown) to the film unit. For example, the timer can be started when the sampling rings are immersed into the assay fluid. Following the prescribed time period for generating luminescent reactions, as indicated by the timing device, the sample carrier is rotated to the film exposing position. During rotation, the opening pin engages the shutter and drives the latter to its unblocking condition, while the closing pin correspondingly disengages the shutter; whereby the film aperture is opened so that the film can be exposed. It will be understood that displacement stops (not shown) for controlling displacement of the sample carrier can be appropriately provided. Accordingly, the film can be exposed by luminescent activity, assuming one, of course, occurs. The time interval for such an exposure can vary upon several factors including the speed of the film. Actuation of the timer 100 can occur manually or even automatically as, for example, in response to movement of the sample carrier by carrier drive means (not shown). The present invention envisions the use of film printable devices, such as LED's (not shown) that would be attached to the housing and otherwise actuatable to record desired information.

To process the latent luminescent images on the film, the film tab is pulled, whereby the film unit emerges from the housing through the processing rollers. As a result thereof, processing of the film units is initiated. Because of the frangible connection between each of the units, the unit pulled from the device separates and the next successive film unit is indexed to the exposure position for another test as a result of the pulling action on the strip. For instance, the test will indicate either a positive or negative result in a manner that is quickly and easily ascertained. The result is simple to read and understand and is one that does not require user interpretation, such as determining the color of a test result or calculating any quantification. It will be appreciated that as a consequence, a safe and simple diagnostic test is performed that provides a positive record of the test being conducted. Such testing is of particular benefit, particularly in the home testing market wherein it can be used for a variety of diagnostic tests with a certainty of results and a significant ease of operation.

As shown in FIG. 3, the sample carrier barrel need not have the opening and closing pins acting in cooperation with a shutter and, in fact, does not cooperate with a shutter. Rather, the sample carrier barrel, in effect, acts as a shutter. Towards this particular end, a bottom surface of the barrel is covered by a light-blocking material 98 that has a low-coefficient of friction, such as felt. While felt is disclosed in this embodiment, the present invention envisions a variety of materials that can be used in an equivalent manner. An opening in the felt is coincident with the passage 56. The felt or other similar materials provide obviate the need for a shutter and shutter actuating mechanism. In addition, the present invention contemplates the use of a solenoid actuated shutter that would be operated by a suitable energizing means and provide somewhat greater control over the shuttering functions.

Figure 4:
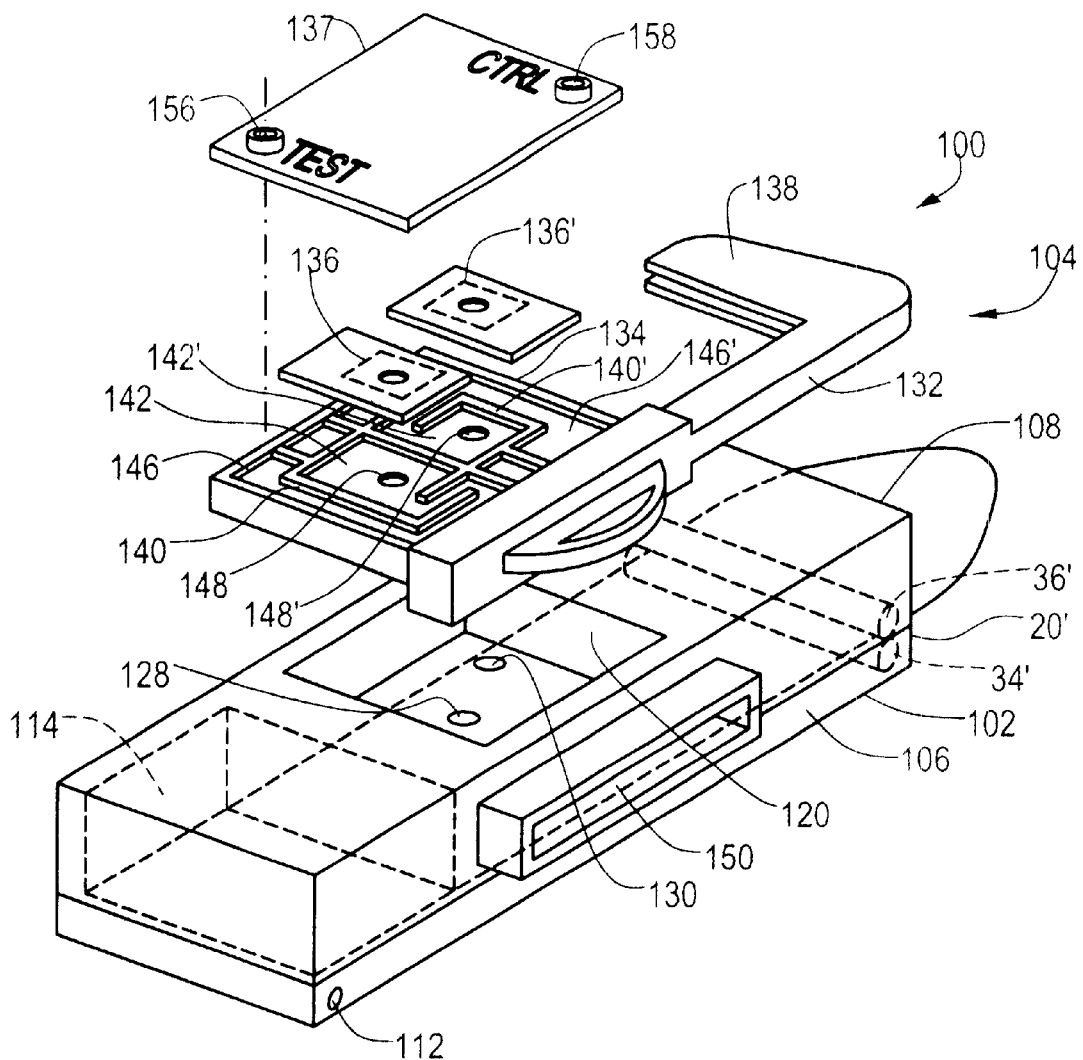
FIG. 4 is a bottom plan view of alternate embodiment of a sample carrier.
Figure 5:
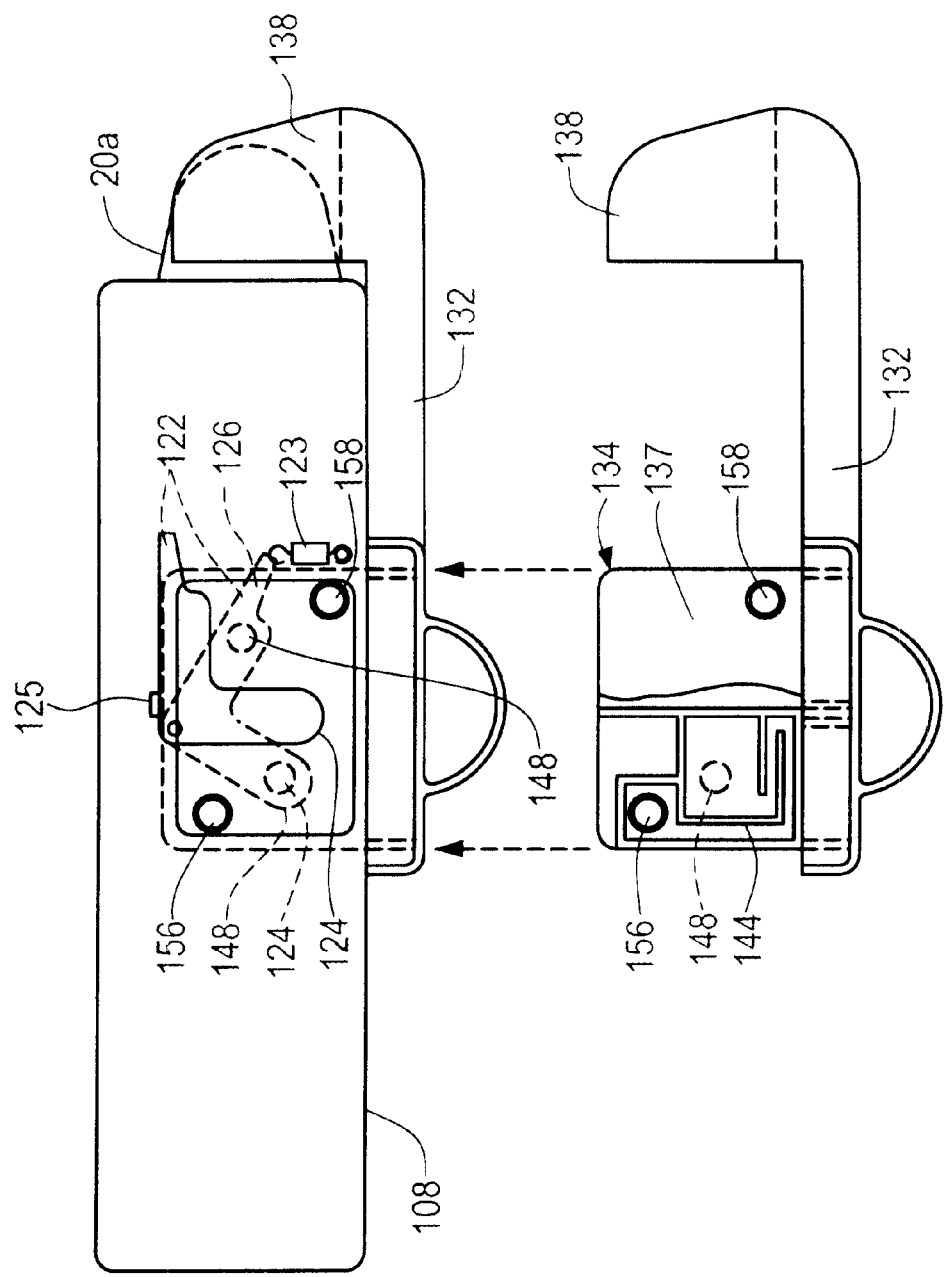
FIG. 5 is a view of an alternate embodiment of a diagnostic assay system of the present invention.

Reference is made to FIGS. 4 and 5 for illustrating another preferred embodiment of a multiple-sample processor 100 made according to the present invention. Structure of this embodiment similar to that of the previous embodiment will be indicated by like reference numerals with the addition of a prime mark. The sample processor 100 includes a housing assembly 102 and a sample carrier assembly 104 that are cooperable with each other in a manner to be described. Included in the housing are generally rectangular and matable lower and upper processor portions 106 and 108 which form a light-tight enclosure for housing a film assemblage 20' like that described last-noted embodiment. Accordingly, a leading one of the film units is in a position for exposure within the housing and its tab 20a protrudes. The housing portions are hingedly connected as at 112 to permit loading of a film box 114 that is loadable within a complementary shaped compartment within the housing. The housing assembly 102 is, preferably, dimensioned to be hand-held and portable for convenient use in the field. The housing portions are made of any material suitable to define, preferably, a light-tight enclosure. While a hinged coupling is described, a wide variety of approaches for joining the two opposed housing components are envisioned. The lower processor housing portion 106 is similar in construction to that described in the last-noted application. Basically, it includes a film supporting wall (not shown) a processing fluid spreading structure 30' (not shown) for spreading the processing fluid ruptured from the pod in a well-known manner. A lower spread roller 34' is rotatably supported in the lower housing portion for cooperating with a biased upper spread roller 36' in the upper housing portion 28 to define a pressure nip. The spread rollers serve to rupture the pod and spread the processing fluid. In addition, the nip thereof acts to inexpensively retain the film assemblage within the housing prior to use of the device. Accordingly, the film can be transported and handled without fear of it becoming dislodged or otherwise separated.

The upper housing 108 has a generally parallelepiped construction with a generally rectangular recess 120 and houses generally a pivoting shutter plate 122 having a pair of light blocking arms 124 and 126 that are selectively movable with respect to openings 128 and 130 in the bottom of the well. The shutter plate 122 is resiliently biased by a spring 123 to a solid line position with respect to the housing so as to be in a light-blocking relationship to the film whereby, the film openings 128, 130 are not in registry with the openings 148 and 148'; respectively. The shutter plate is movable to a light-unblocking relationship when the carrier is inserted within the processor so that the openings 128 and 130 will be in registry with the openings 148 and 148'; as will be described.

The sample carrier assembly 104 includes an elongate handle portion 132, an assay holder tray 134, for holding assay test strips 136, 136', a tray cover 137, and a tab guide 138. The holder tray 134 and cover are removably held within a recess formed in the handle 132 and held by means of a frictional fit or other suitable means. In this embodiment, the upper surface of the tray includes, preferably, a pair of molded grooved arrangements 140, 140'. The molded grooved arrangement 140 is for the test sample and the arrangement 140' is for allowing the performance of a control test being conducted with the test sample. Each one of which defines a generally rectangular test strip receiving well 142, 142'. Since both grooved arrangements are identical in construction, only the structure of one will be described. The receiving well 142 is in fluid communication with a capillary type fluid delivery channel 144 that is, in turn, in fluid communication with test fluid reservoir 146. The reservoir 146 is for receiving a biological test fluid introduced therein by any suitable means, such as a pipette; not forming a part of this invention. A light transmitting aperture 148 in the well 142 is in optical registry with the opening 128 and thus with the image recording area of the film when the shutter blade is in its exposing position. Movement of the shutter blade to its opening position occurs in response to the tray engaging a resiliently bendable tab 125 (FIG. 5) as the tray is inserted into a rectangular opening 150 formed in a side of the housing assembly and overcoming the bias of the spring. The test strip 136 is a suitably dimensioned chemiluminescent testing assembly or assay test strip for interacting with a preselected reagent, such as an analyte. The analyte is carried in a biological fluid test sample that is delivered to the reservoir and from the reservoir via the fluid delivery channel 144 to the test strip. The test strip can be constructed from any of a wide variety of materials so long as it generates a luminescent signal capable of being recorded on film in response to interacting with a reagent carried in the test fluid. The capillary delivery channel 144 is comprised of a labyrinth grooved construction that is molded in the upper surface and serves to transfer the test fluid sample in a light-tight relationship from the reservoir to the well by virtue of capillary action. Therefore, it will be appreciated that the delivery channel 144 is constructed and dimensioned to induce or allow capillary action to transfer the test fluid from the reservoir to the well. In this embodiment, the walls defining the delivery channel 144 have a depth in the order of about 0.005 inch to 0.0024 inch in order to transfer the fluid by virtue of capillary action. The fluid reservoir 146 is of sufficient size to accommodate the quantity of test fluid to be deposited therein and, as noted, is in fluid communication with the channel 144. The cover 137 is generally rectangular and has a fluid reservoir opening 156 in covering relationship to the grooved arrangements 140, while a fluid port 158 is in communication with the grooved arrangement 140' for delivering the control fluid. The control fluid will yield a chemiluminescent response with the assay strip 136'.

The cover 137 is suitably joined, as by heat bonding or ultrasonic welding to the tray. The fluid opening 156 is in direct fluid communication with the reservoir 146 for allowing delivery of the test fluid, as by a pipette, to the reservoir. The cover 137 can, if desired, be removably joined to the upper housing portion should it be so desired. In addition to the capillary action provided by the channels, the present invention contemplates that use of a wicking device made of suitable material (not shown) that can be added to the channels 144, 144' to assist in transferring the test fluid. It is equally clear that the present invention envisions substituting a wicking system for the capillary channel itself. While one particular molded arrangement is illustrated for effecting the capillary flow, a wide variety of configurations and dimensions can be used for transferring the fluid. It is further envisioned that other than liquid actuated systems are contemplated, such as gaseous mediums. The tab guide 138 includes two spaced apart semi-circular parts that are adapted to surround the protruding tab 20a so as to inhibit the user pulling on the film unit until exposure is complete as determined by the type of chemiluminescent reaction occurring. Of course, suitable timing and/or printing mechanisms can be provided either in an integrated fashion with the device or separate therefrom. Removal of the test sample carrier allows the user to pull on the tab and commence processing of the latent image(s) on the film. Also the shutter returns to the light blocking condition and the tab 20a returns to a position which allows it to be engaged by the tray.

After explaining the construction, the operation thereof is self-evident. However, the following brief description of the operation is provided as a supplement. An operator introduces a test fluid sample through the reservoir opening 156, as by a pipette, into the reservoir. The test fluid sample is transferred by reason of the capillary action induced by the capillary channel 144 to the test strip. If the test fluid contains the analyte being tested for, a chemiluminescent reaction occurs after a prescribed period of time. This generated signal transmitted to the film through the aligned openings 148, 128, 124 for effecting exposure. As long as the carrier remains inserted, a light-tight condition exists for proper exposure.

In order to process the latent image, the protruding tab 20 is pulled after the noted prescribed period of time, for example sixty (60) seconds. As noted, the pressure applying rollers rupture the pod and spread the fluid to develop any latent image generated by the chemiluminesence. Although a pair of a test strips is shown, additional tests with additional assay strips can be provided.

Figure 6:
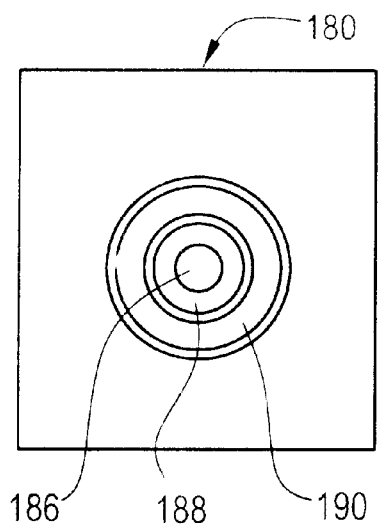
FIG. 6 is an enlarged schematic view of the interaction between the a sample carrier and a shutter mechanism.
Figure 7:
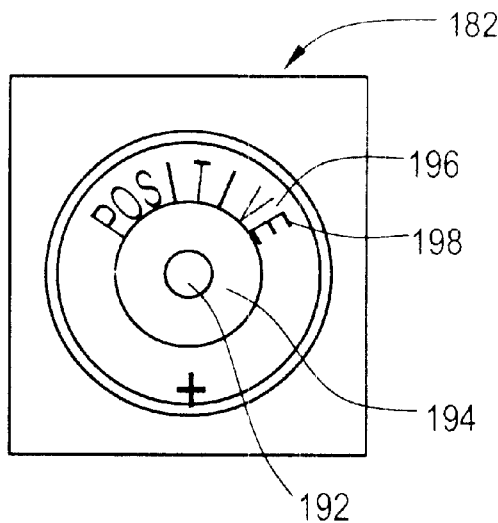
FIG. 7 is a plan view of an optical filtering arrangement for use in the diagnostic assay systems.

FIGS. 6 and 7 schematically depict use of an optical filtering arrangements 180, 182; respectively, for quantifying the results of the luminescent signals that are provided. In this embodiment, the filtering arrangement 180 comprises a flat filtering disk adapted to be positioned under the exposure aperture and is operable, in combination with the generated luminescent signals, for showing different light values on the film. In this embodiment, provision is made for three neutral density filters 186, 188 and 190 arranged as depicted that are separated and have decreasing transmissivity (e.g., 1 or 2 stops) characteristics to the light. Filter 186 is selected to allow the most light to the film and the filters 188 and 190 are graduated to require increasingly higher light levels to pass on the film. It will be appreciated that the higher the light level generated the greater the chemiluminescent activity is produced. Thus, the size of the chemiluminescent image will be proportional to the intensity of the reaction. In this manner, the chemiluminescent activity can be quantified by its size to indicate, for example, the degree to which a surface is contaminated by microorganisms.

FIG. 7 depicts another embodiment of an optical filtering arrangement 182 that is particularly adapted for use as an overlay to the film that is being exposed. The filter includes a transmissive center 192, an opaque ring 194, a transparent ring 196 with indicia 198 thereon in combination with the devices of the present invention. The filter inclues when compared to the alternating transparent rings 184, 186 and filtered rings 188, 190. Indicia 192, such as the term "positive" can be printed on the transparent rings, so as to assist the user in proper assessment of the test results. In this embodiment, the filter rings can be made neutral density filters that have light attenuating characteristics in the order of about one (1) or two (2) stops. The light attenuating characteristics can, of course, vary depending on the amount of light that is anticipated to be generated. Thus, if a relatively small spot is generated and appears visible only through the center only, such might be indicative of test results that are inconclusive; thereby requiring the performance of additional tests. If of course, no signal is generated, then the test is negative. If there is a sufficient signal, it will generate a spot visible through the transparent ring. While the foregoing embodiment discloses use of neutral density filters, the present invention is not so limited and encompasses other optical filtering arrangements. Although not shown, the present invention contemplates having the film pre-exposed with images, such as spots, having different sizes. The sizes would generally correlate to the size of spots that would be produced by luminescent signals indicative of, for example, the intensity of the ATP reaction in a test sample. This would assist in the quantificaion of test outputs. Alternatively, an overlay (not shown) could be placed over the film with, for example, the same type of spot gradation in order to compare the test signal exposure spot with these pre-exposed spots in order to assist in the quantification of the resultant luminescent signal.

Figure 8:
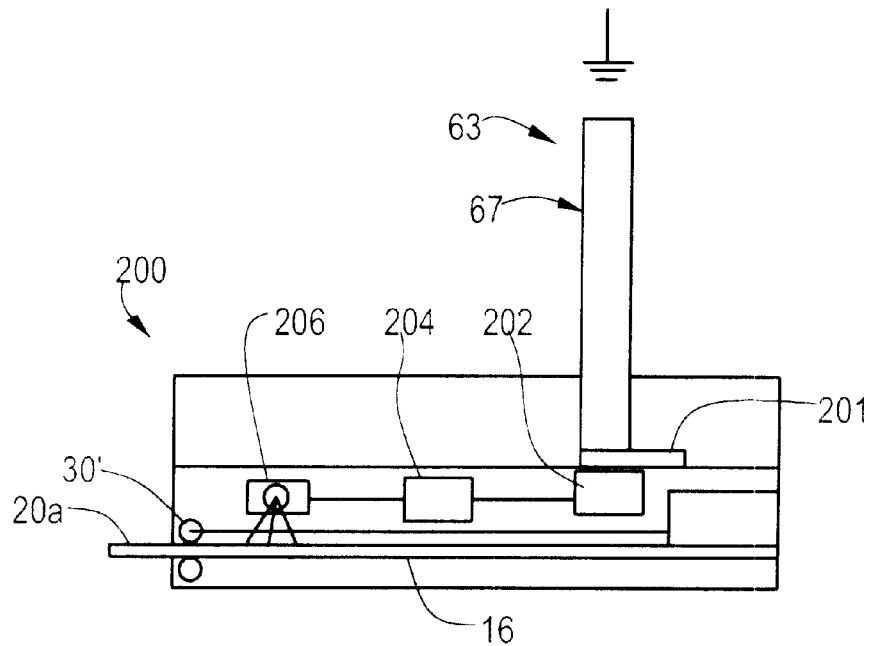
FIG. 8 is a plan view of another embodiment of an filtering arrangement.

FIG. 8 illustrates schematically another embodiment of the versatile, hand-held assay system 200. In this version, however, the luminescent read-out signal of the ampoule, for example, is read by any suitable solid-state photodetector, such as a CCD 202. The exposure of the CCD is under the control of a shutter mechanism 201, which may be of the electromagnetic type. The CCD 202 is placed beneath the ampoule and in registration to the exposure aperture and is operably connected to a print driver in print head controller 204 that drives a light source in a light-tight enclosure; such as a plurality of LED's 206. Operation of the LED's 206 exposes a film units of a film assemblage 16. The LED's for instance, can be illuminated to provide qualitative and quantitative information which is sensed from the CCD 202. For example, LED patterns indicative of the relative strength of the luminescent signal can be printed on the film. The exposed film unit is processed as indicated previously. Other light and image forming sources can be used, such as LCD's or vacuum florescent tubes for printing a variety of information. Also, other control devices, such as a microprocessor can be used in a variety of ways.

Figure 10:
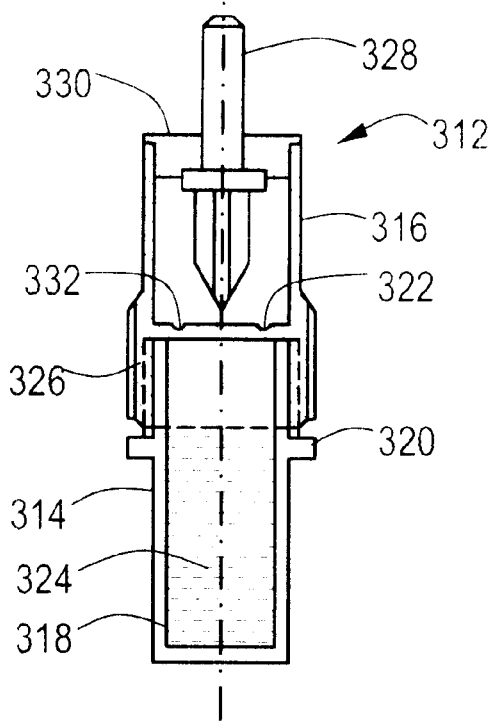
Figure 9:
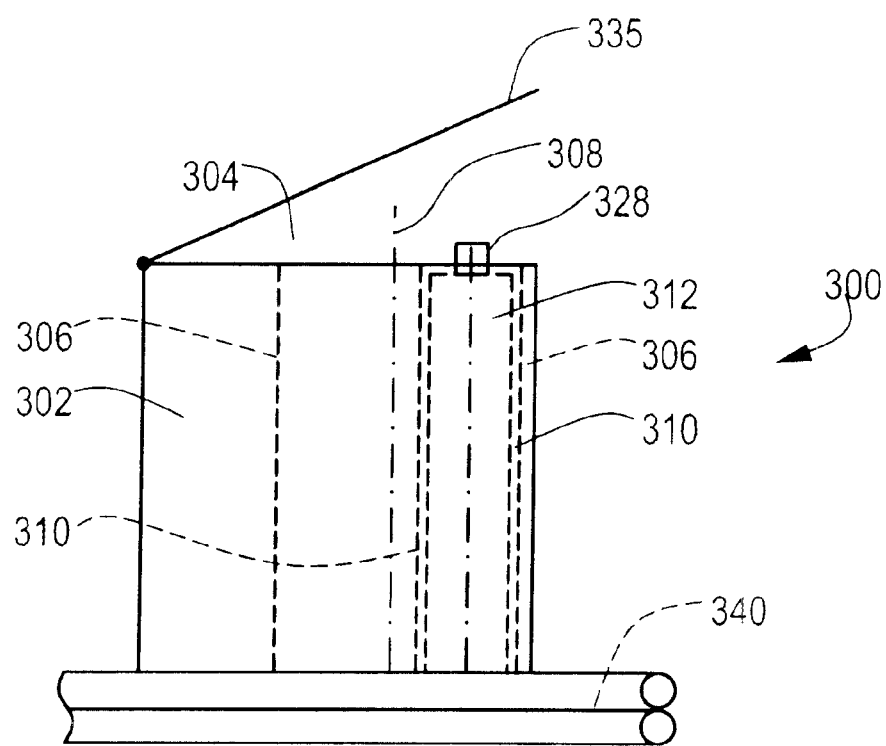
FIG. 9 is a schematic view of yet another preferred embodiment of a processor of the present invention; and, FIG. 10 is a cross-sectional view of a test container usable in the processor of FIG. 9.

FIGS. 9 and 10 illustrate yet another preferred embodiment of the present invention. FIG. 9 illustrates a processor 300 which includes a light-tight housing 302 having an open top end 304 in which is rotatable a barrel 306 similar to that which is described in the first embodiment. This version is rotatable, preferably manually, about vertical axis 308. The barrel 306 includes a plurality of openings 310, one of which is illustrated. Each of the openings 310 is adapted to removably receive a generally cylindrical test container assembly 312. The test container 312 comprises in essence to lower and upper reservoirs 314 and 316; respectively. The reservoirs are made of a suitable material such as plastic. The reservoir 314 includes a transparent cylindrical closed end wall 318 that allows the luminescent signal to pass therethrough and expose the film through the bottom opening of the barrel. The reservoir 314 includes a mounting flange 320 that is adapted to seat against complementary structure (not shown) within an opening 310. A penetrable sealing membrane 322 made of a suitable material such as described above covers the open end of the reservoir 314. A luminescent testing fluid 324 is sealingly housed in the lower reservoir 314.

The upper reservoir 316 has a cylindrical configuration with an open end that is threadedly fastened as at 326 to the exterior surface of the open end of the lower reservoir 314. An actuator member 328 protrudes from one end of the upper reservoir 316 and is adapted to be slidable within an end plug 330. The upper reservoir 316 holds a fluid 332 capable of mixing with an analyte of interest obtained through sampling in a manner to be described. The actuator member 328 is adapted to be urged into the reservoir, as when the cover 335 closes the upper end of the housing 302 so that its tip will penetrate the membrane 322. This action thereby allows the fluid 322 that has been mixed with the analyte of interest to flow by gravity into the reservoir 314 wherein they react with the testing fluid 324. Consequently, should a chemiluminescent reaction occur it will be transmitted through the opening to the film or any other suitable image recording assembly, such as a CCD.

In use, an operator would separate the reservoirs by unfastening them. The operator would after taking a test sample, such as by swabbing a patient's throat insert the swab into the fluid contained in the upper reservoir and then reconnect the two reservoirs. A test container would be inserted into one of the openings 310 in the barrel 302, so that the transparent wall 318 is seated in close proximity to the bottom of the barrel. The barrel is rotated so that the bottom of each of the respective openings 310 is in registry with a corresponding aperture (not shown) in the bottom wall of the housing. The apertures are in optical communication with the film; which is preferably of the self-developing type. As noted there is a light-tight relationship between the barrel and the housing apertures. When the cover 335 is closed it drives the actuator 328 downwardly sufficiently to penetrate the membrane 322. This allows the fluid in the upper reservoir to mix with the fluid 324 in the lower reservoir for commencing a chemiluminescent reaction. Closing of the cover 335 can also serve to prevent removal of the film through any suitable interlock (not shown) with a film advancing system not shown but well-known in the field of processing self-developing film units. It will be appreciated that motor controls can be provided to this system for rotating the barrel. The barrel when rotated can actuate a switch to in turn actuate a locking device (not shown) that locks the cover and or barrel in place thereby preventing premature removal of the test container or movement of the barrel. As noted a suitable interlock can prevent premature withdrawal of the film until a predetermined time has elapsed.

Although the foregoing invention has been described in some detail, it will be readily apparent to those of ordinary skill in the art that certain changes and modifications may be made thereto without departing from the spirit and scope of the appended claims.

What is claimed is:

1. A portable diagnostic assay system for conducting a luminescent test and recording luminescent signals generated thereby on an image recording material, the system comprising:

a processor including a portable, hand-held and light-tight housing having first and second openings, and a shutter mechanism within the housing and being located at an exposure station so as to be operable for operation between unblocking and blocking conditions relative to at least one exposing aperture in response to corresponding insertion and removal of a removable sample carrier from the housing; and, a fluid processing assembly in the housing for processing self-developing film units;

at least one luminescent testing assembly capable of generating a luminescent activity;

a sample carrier that carries the testing assembly and is insertable in and withdrawable from the second opening for operating;

said sample carrier being constructed to activate the shutter mechanism to the unblocking condition when inserted into the second opening, and allow the shutter mechanism to return to the blocking condition when removed from the second opening; whereby when the shutter mechanism is in the unblocking condition a luminescent reaction conducted on the film assemblage can expose the film through the exposure aperture; and, an image recording assemblage is housed in the processor at the exposure station.

2. The system of claim 1 wherein image recording assemblage is a self-developing integral film unit having an image recording area and a pod of processing fluid, the film unit is housed in the processor at the exposure station; and is capable of being processed as it advances from the housing.

3. The system of claim 2 wherein the film assemblage has a leading portion thereof extending from the first opening in the housing; and the assemblage is pullable from the first opening so that the exposed image area thereof can be have its latent image processed by the fluid processing means as the assemblage is pulled from the housing.

4. A hand-held, portable diagnostic assay system for conducting and recording luminescent reactions that generate luminescent read-out signals which are recordable on an image recording medium, the system includes a housing assembly defining a light-tight enclosure carrying at least the image recording medium, and an exposure opening that optically communicates the recording medium with the luminescent signal; a carrier assembly has one condition for receiving a luminescent testing assembly that is capable of generating the luminescent read-out signal recordable on the recording medium through the exposure opening, and a second condition in which the carrier assembly is inserted through an opening in the housing into the enclosure for allowing the recording medium to be exposed with the luminescent signal, wherein said test assembly includes a container having a transparent bottom portion that is insertable into an opening in the carrier assembly, the carrier assembly opening being out of optical communication with the exposure opening when the carrier assembly is in the first condition and in optical communication when the carrier assembly is in the second condition, whereby a luminescent signal is recordable on the recording medium when the carrier assembly is in its second condition, and wherein said test container comprises a reservoir that stores a luminescent testing fluid that is sealed by a sealing membrane; and, a sample testing device which contains a sample to be tested and is inserted into the container such that it penetrates the sealing membrane such that the sample testing device cooperates with the sample fluid.

5. The system of claim 4 further including a shuttering mechanism in operative relationship to the enclosure and which moves into an exposing condition relative to the exposure opening when the carrier is inserted into the enclosure and returns to a light blocking condition relative to the exposure opening when the carrier is removed from the enclosure.

6. The system of claim 5 wherein the image recording medium is a self-developing film unit which is processed as the film unit is advanced from the housing after passing therethrough.

7. The system of claim 4 wherein the luminescent testing assembly includes a sampling device which can sample a surface to be tested and then be inserted, in a light-tight manner, within the test container such that a portion thereof penetrates the membrane and is immersed in the fluid.

8. The system of claim 4 wherein the carrier assembly is rotatable in the housing from the first condition wherein the transparent reservoir portion is out of registry with the exposure opening and the exposure opening is blocked from light to the second condition wherein the transparent reservoir portion is in optical communication to the exposure opening for exposing the film.

9. The system of claim 8 wherein the carrier assembly includes a cover member movable from a position for allowing the fluid container to be inserted into the carrier assembly opening to a light-tight position over the fluid container, wherein the cover member causes an actuating member of the fluid container to penetrate the sealing membrane so that fluid of one reservoir in the fluid container can mix with the luminescent testing fluid for generating the read-out signal.

10. The system of claim 8 wherein the fluid container includes first and second separable reservoirs, the first contains the luminescent testing fluid and is sealed by the sealing membrane, the first reservoir includes transparent walls for allowing a luminescent read-out signal to expose the image recording medium; the second reservoir includes an actuating element at one end thereof, the second reservoir being separable from the first reservoir and contains a fluid into which a reagent of interest can be inserted, such that the actuating element when actuated penetrates the membrane to allow the fluid and analyte of interest to mix with the testing fluid for commencing a luminescent reaction.

11. The system of claim 4 further including means for effecting and recording a luminescent read-out signal of a control test in addition to the luminescent read-out signal of a test sample.

12. The system of claim 4 wherein the carrier assembly carries the luminescent sample test assembly and a luminescent control test assembly, the carrier assembly also includes fluid transfer means for allowing transfer of the control and test fluids; respectively, from separate ports in the housing to the respective test assemblies.

13. The system of claim 12 wherein the fluid transfer means comprises capillary grooves in a light-tight arrangement.

14. The system of claim 4, further including means for quantifying the luminescent read-out signal generated and recorded on the film.

15. The system of claim 14 wherein the quantifying means includes an optical filter element comprising a series of alternating transparent and opaque zones that act to delineate different sized read-out signals; whereby different sized developed latent images correlate to corresponding different test results, thereby providing a visual measurement of the test results.

16. The system of claim 15 wherein the quantifying means includes a series of existing symbols of different sizes on the film wherein each size corresponds to a different strength of a read-out signal, so that the read-out signal captured by the test can be compared to the different symbols.

* * * * *